US010550086B1

(12) United States Patent
Sugiyama et al.

(10) Patent No.: US 10,550,086 B1
(45) Date of Patent: Feb. 4, 2020

(54) LENVATINIB DERIVATIVE, AND COMPOSITION FOR PHARMACEUTICAL RESEARCH AND TUMOR THERAPEUTIC AGENT USING THE SAME

(71) Applicant: Institute of Applied Biochemistry, Kani-gun, Gifu Prefecture (JP)

(72) Inventors: Satoru Sugiyama, Kani-gun (JP); Katsuhiro Hayashi, Kani-gun (JP)

(73) Assignee: INSTITUTE OF APPLIED BIOCHEMISTRY, Kani-Gun, Gifu Prefecture (JP)

( * ) Notice: Subject to any disclaimer, the term of this patent is extended or adjusted under 35 U.S.C. 154(b) by 0 days.

(21) Appl. No.: 16/360,528

(22) Filed: Mar. 21, 2019

(30) Foreign Application Priority Data

Dec. 25, 2018 (JP) ................................ 2018-240852

(51) Int. Cl.
*C07D 215/48* (2006.01)
*A61P 35/00* (2006.01)

(52) U.S. Cl.
CPC ............ *C07D 215/48* (2013.01); *A61P 35/00* (2018.01)

(58) Field of Classification Search
CPC .................................................. C07D 215/48
See application file for complete search history.

(56) References Cited

U.S. PATENT DOCUMENTS

| 6,187,926 B1 | 2/2001 | Osawa et al. |
| 2004/0053908 A1 | 3/2004 | Funahashi et al. |
| 2004/0209905 A1 | 10/2004 | Kubo et al. |

FOREIGN PATENT DOCUMENTS

| JP | 52-122373 A | 10/1997 |
| WO | WO 98/47873 A1 | 10/1998 |
| WO | WO 00/43366 A1 | 7/2000 |

OTHER PUBLICATIONS

Kajimoto, Katsuya, "Function of vasodilating agent in treatment of acute heart failure syndromes", Heart's Selection 3, vol. 44, No. 5, 2012, pp. 534-539.
Keshet et al., "Arginine and the metabolic regulation of nitric oxide synthesis in cancer", Disease Models & Mechanisms, vol. 11, No. 8, 2018, pp. 1-11.
Kodela et al., "NOSH-aspirin (NBS-1120), a novel nitric oxide- and hydrogen sulfide-releasing hybrid has enhanced chemo-preventive properties compared to aspirin, is gastrointestinal safe with all the classic therapeutic indications", Biochemical Pharmacology, vol. 98, No. 4, Dec. 2015, 20 pages.
Patil et al., "Synthesis of Nicorandil: An Antianginal Agent", Indian Journal of Pharmaceutical Sciences, Sep.-Oct. 1999, pp. 304-305.
Price et al., "4, 7-Dichloroquinoline", Organic Synthesis Collective, vol. 3, 1955, pp. 272-274.
Riganti et al., "Mitochondrial-targeting nitrooxy-doxorubicin: a new approach to overcome drug resistance", Molecular Pharmaceutics, vol. 10, No. 1, 2013, 60 pages.
Satoh et al., "Cardiovascular actions of a new coronary vasodilator drug, 2-nicotinamidethyl nitrate (SG-75)", Heart, vol. 12, No. 4, 1980, pp. 371-380, No English Translation Provided.
Shimizu et al., "Hypotensive and Hemodynamic Effects of Nipradilol in Hypertensive Rats", Japanese Pharmacology & Therapeutics, vol. 14, No. 2, Feb. 1986, pp. 609-623, No English Translation Provided.
Takahashi, Shunji, "Multi-target tyrosine kinase inhibitor, Multi-TKI", Journal of Molecular Targeted Therapy for Cancer, vol. 14, No. 3, 2016, pp. 301-307.
Tsuruoka et al., "Preclinical and clinical researches of lenvatinib mesylate (Lenvima capsule), a novel antitumor agent approved for thyroid cancer treatment", Folia Pharmacologica Japonica, vol. 146, No. 5, 2015, pp. 283-290, No English Translation Provided.
Yano, Seiji, "Recent trends of cancer treatment by targeted drugs", Head and Neck Surgery, vol. 25, No. 3, 2015, pp. 259-263.
Machine English translation of JP 52-122373 published Oct. 14, 1977.
Partial English tranlation of Kajimoto, Katsuya, "Function of vasolidating agent in treatment of acute heart failure syndromes," Heart's Selection 3, vol. 44, No. 5, 2012, pp. 534-539.
Partial English translation of SATOH et al., "Cardiovascular actions of a new coronary vasodilator drug, 2-nicotinamidethyl nitrate (SG-75)", Heart, vol. 12, No. 4, 1980, pp. 371-380.
Partial English translation of Shimizu et al., "Hypotensive and Hemodynamic Effects of Nipradilol in Hypertensive Rats", Japanese Pharmacology & Therapeutics, vol. 14, No. 2, Feb. 1986, pp. 609-623.
Partial English translation of Tsuruoka et al., "Preclinical and clinical researches of lenvatinib mesylate (Lenvima capsule), a novel antitumor agent approved for thyroid cancer treatment", Folia Pharmacologica Japonica, vol. 146, No. 5, 2015, pp. 283-290.

*Primary Examiner* — Laura L Stockton
(74) *Attorney, Agent, or Firm* — Birch, Stewart, Kolasch & Birch, LLP

(57) ABSTRACT

To provide a compound and a tumor therapeutic agent which are highly effective in cancer therapy and are less likely to cause hypertension as a side effect, and to provide development of a drug for elucidating the action mechanism of lenvatinib to help further development of new drugs.
The lenvatinib derivative of the present invention comprises a compound represented by the following chemical structural formula (1) (wherein R represents an alkylene group which may have a branch) and a salt thereof, and a solvate thereof. This derivative has a nitric acid ester group, and thus produces nitric oxide (NO) having a vasodilating action in vivo, so that a higher-concentration lenvatinib component can be expected to arrive at target molecules present in cancer cells and vascular endothelial cells on the host side and also can suppress hypertension as a side effect.

3 Claims, 5 Drawing Sheets

FIG. 4  Metabolic pathway of lenvatinib 4-10
(wherein R is an ethylene group)

LENVATINIB DERIVATIVE, AND COMPOSITION FOR PHARMACEUTICAL RESEARCH AND TUMOR THERAPEUTIC AGENT USING THE SAME

BACKGROUND OF THE INVENTION

(1) Field of the Invention

The present invention relates to a lenvatinib derivative, and a composition for pharmaceutical research and a tumor therapeutic agent using the same.

(2) Description of Related Art

In recent years, with the progress of molecular biology, molecularly targeted drugs targeting proteins corresponding to genes involved in carcinogenesis and cancer progression have attracted attention, and the development thereof is under way. Among these molecularly targeted drugs, low-molecular-weight tyrosine kinase inhibitors (TKIs) can selectively inhibit various tyrosine kinases, which are important in transmitting a signal of cell proliferation, to lower the proliferative capacity of cancer cells.

Many tyrosine kinase inhibitors inhibit a plurality of tyrosine kinases as targets, and are therefore called multi-target tyrosine kinase inhibitors (multi-TKIs). As examples of multi-TKIs, there are known imatinib (target molecules: Bcr-Abl tyrosine kinase (Bcr-Abl), platelet-derived growth factor (PDGFR), c-Kit receptor tyrosine kinase (KIT); adaptation diseases: chronic myelogenous leukemia, KIT-positive gastrointestinal stromal tumor, etc.), sorafenib (target molecules: vascular endothelial growth factor receptor (VEGFR), PDGFR, Fms-like tyrosine kinase 3 (Flt 3), KIT, RAF protein kinase (Raf); adaptation diseases: progressive kidney cancer, progressive liver cancer, differentiated thyroid cancer), lenvatinib, and the like.

Among these multi-target tyrosine kinase inhibitors, lenvatinib represented by the following chemical formula (a) inhibits rearranged during transfection cancer gene (RET), KIT, PDGFR, c-Met tyrosine kinase (c-Met), and the like, in addition to VEGFR and fibroblast growth factor (FGFR) involved in tumor angiogenesis. In a Phase I clinical trial, lenvatinib is observed to have a tumor shrinkage effect in thyroid cancer, endometrial cancer, melanoma, renal cell carcinoma, soft tissue sarcoma, colon cancer, ovarian cancer, and pancreatic cancer. As a pharmaceutical product, lenvatinib is applied as a therapeutic agent for radically unresectable thyroid cancer and unresectable hepatocellular carcinoma (Journal of Molecular Targeted Therapy for Cancer, Vol. 14, No. 3, pp. 301-307, 2016; Journal of Japan Society for Head and Neck Surgery, Vol. 25, No. 3, pp. 259-263, 2016; and Folia Pharmacologica Japonica, Vol. 146, No. 5, pp. 283-290, 2015).

[Chemical Formula 1]

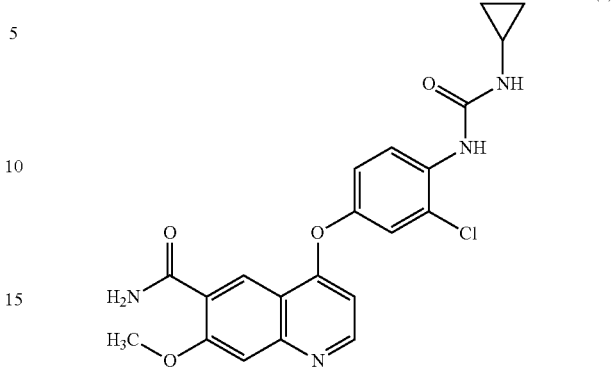

(a)

On the other hand, nitric acid drugs such as nitroglycerin, isosorbide nitrate, and nicorandil (see the following chemical formula (b)) are known as vasodilators to be applied to angina pectoris, acute heart failure, and the like. Nitric acid drugs release nitric oxide (NO) in vivo, and NO stimulates guanylate cyclase in vascular smooth muscle cells to dilate blood vessels. In the heart, NO increases blood flow to the heart by dilation of the coronary artery to suppress anginal attacks, and also has an action of reducing the burden on the heart by dilation of peripheral blood vessels (both arteries and veins) (Heart, Vol. 44, No. 5, pp. 534-539, 2012 and Heart, Vol. 12, No. 4, pp. 371-380, 1980). Nipradilol having a nitric acid ester group, similarly to nicorandil, has a hypotensive action (Japanese Pharmacology & Therapeutics, Vol. 14, No. 2, pp. 609-623, 1986) and is applied to essential hypertension, and compounds into which functional groups generating NO in vivo, such as nitro groups and nitric acid esters, have been introduced are expected to have a blood flow increase action and a hypotensive action due to vasodilation.

[Chemical Formula 2]

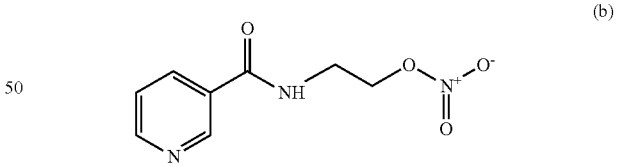

(b)

The action of NO in tumors has two aspects, and the results have been reported that, depending on the NO concentration in the tumor microenvironment, NO exhibits tumor growth and tumor exacerbation in some cases, and exhibits oxidative DNA damage, apoptosis induction, mitochondrial energy metabolic disorder, anti-angiogenic effect, and antitumor actions such as host immune system action on tumors in other cases (Disease Models & Mechanisms, Vol. 11, No. 8, page dmm033332, 2018). Good results such as reduction in tumor growth and overcoming of drug resistance have been obtained by the addition of NO releasing agents, aspirin-ONO2 (Biochemical Pharmacology, Vol. 98, No. 4, pp. 564-572, 2015) and Nitrooxy-doxorubicin (Molecular Pharmaceutics, Vol. 10, No. 1, pp. 161-174, 2013).

SUMMARY OF THE INVENTION

Lenvatinib is advantageously excellent in therapeutic effect, because of its high selectivity to cancer cells, as compared with conventional cytotoxic antitumor agents. Also, it can be advantageously applied to surgically unresectable refractory cancers. However, lenvatinib has a side effect of causing hypertension (Journal of Molecular Targeted Therapy for Cancer, Vol. 14, No. 3, pp. 301-307, 2016 and Folia Pharmacologica Japonica, Vol. 146, No. 5, pp. 283-290, 2015), and the improvement of this adverse event has been demanded. Further improvement of the cancer therapeutic effect has also been demanded. Furthermore, it has been demanded to develop a drug serving as a tool for elucidating the action mechanism of lenvatinib to help the development of new drugs.

The present invention has been made in view of the above-described conventional actual circumstances, and a problem to be solved by the present invention is to provide a compound and a tumor therapeutic agent which are highly effective in cancer therapy and are less likely to cause hypertension as a side effect. Another problem to be solved by the present invention is to provide a drug serving as a tool for elucidating the action mechanism of lenvatinib to help further development of new drugs.

In order to solve the above problems, the present inventors have considered introduction of a nitric acid ester group into lenvatinib. This is because the nitric acid ester group produces nitric oxide (NO) having a vasodilating action by in vivo metabolism, so that the blood flow is increased, and, as a result, a higher-concentration lenvatinib component arrives at target molecules present in cancer cells and vascular endothelial cells on the host side. Furthermore, this is because NO inhibits the electron transfer cycle of the mitochondria of cancer cells, so that the killing effect of cancer cells can also be expected.

That is, the lenvatinib derivative of the present invention is characterized by comprising a compound represented by the following chemical formula (1) and a salt thereof, and a solvate thereof.

[Chemical Formula 3]

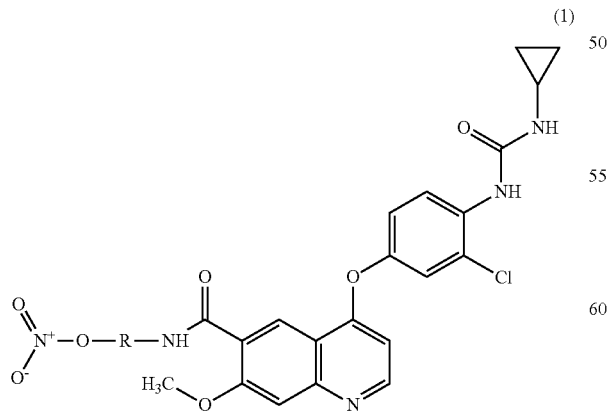

(1)

The lenvatinib derivative of the present invention has a structure in which a nitric acid ester group binds to the amide group binding to the carbon at the 6-position of the quinoline ring present in lenvatinib. Therefore, when this lenvatinib derivative is administered, nitric oxide (NO) having a vasodilating action is produced by in vivo metabolism so that the blood pressure is lowered, thereby providing an effect of preventing hypertension which is a side effect of lenvatinib. In addition, the blood flow is increased by the vasodilating action, so that a higher-concentration lenvatinib derivative can arrive at target molecules present in cancer cells and vascular endothelial cells on the host side. As a result, a high cancer therapeutic effect can be obtained. Furthermore, it serves as a raw material for a suitable pharmaceutical research composition for studying the action mechanism of lenvatinib, such as investigation of the relationship with NO in the in vivo action of lenvatinib.

Therefore, the composition containing the lenvatinib derivative of the present invention serves as a useful composition for pharmaceutical research or a useful tumor therapeutic agent.

DETAILED DESCRIPTION OF PREFERRED EMBODIMENTS

Figure 1:
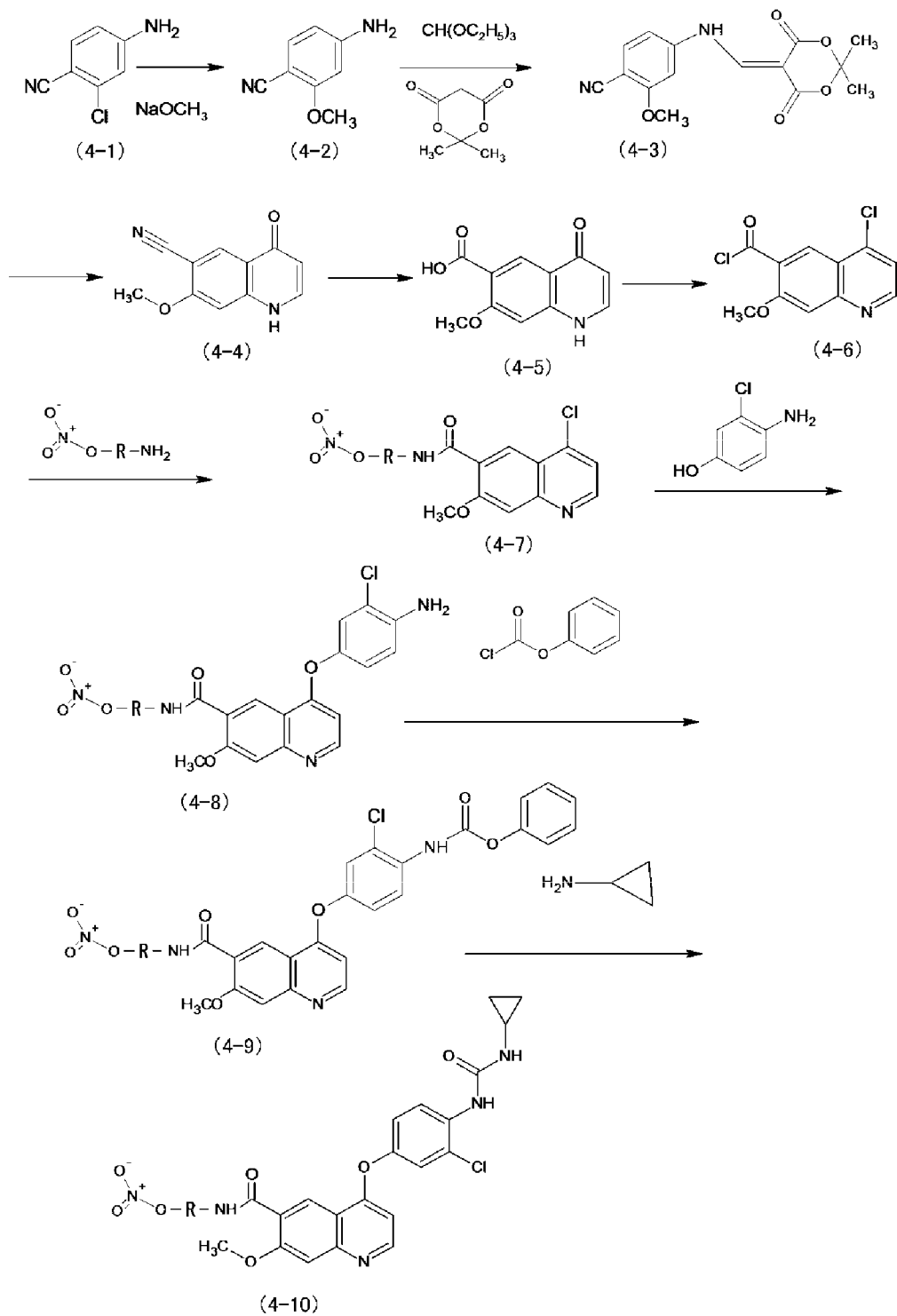
FIG. 1 is a diagram showing a synthetic pathway of a lenvatinib derivative (4-10) of the present invention.

Embodiments of the present invention will now be described.

The lenvatinib derivative of the present invention comprises a compound represented by the following chemical structural formula (1), a salt thereof, and a solvate thereof. In the formula, R represents an alkylene group which may have a branch, and examples thereof include a methylene group, an ethylene group, a propylene group, and an isopropylene group.

[Chemical Formula 4]

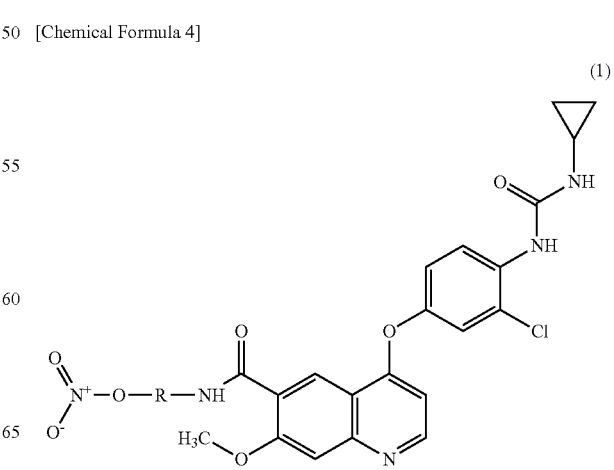

(1)

In addition, the salt is not particularly limited as long as it is a salt exhibiting desired pharmacological activity, and examples thereof include inorganic acid salts such as hydrochloride, hydrobromide, sulfate, nitrate, and phosphate, and organic acid salts such as acetate, propionate, hexanoate, cyclopentanepropionate, glycolate, pyruvate, lactate, oxalate, malonate, succinate, malate, fumarate, tartrate, citrate, benzoate, o-(4-hydroxybenzoyl) benzoate, cinnamate, mandelate, methanesulfonate, ethanesulfonate, 1,2-ethanedisulfonate, 2-hydroxyethanesulfonate, benzenesulfonate, p-chlorobenzenesulfonate, 2-naphthalenesulfonate, p-toluenesulfonate, camphorsulfonate, 4-methylbicyclo [2.2.2]oct-2-ene-1-carboxylate, glucoheptanoate, 4,4'-methylenebis (3-hydroxy-2-ene-1-carboxylate), 3-phenylpropionate, trimethylacetate, tertiary butyl acetate, lauryl sulfate, gluconate, glutamate, hydroxynaphthoate, salicylate, stearate, and muconate.

The tumor therapeutic agent of the present invention can contain, as an active ingredient, the lenvatinib derivative of the present invention alone or as a mixture with any other active therapeutic ingredient. Also, the active ingredient is mixed with one or more pharmacologically acceptable carriers to manufacture the tumor therapeutic agent by any method well known in the art of pharmaceutics.

Various organic or inorganic carrier substances, which are conventionally used as preparation materials, are used as the pharmacologically acceptable carrier, and specific examples thereof include excipients, lubricants, binders, and disintegrants in solid preparations, and solvents, solubilizing agents, suspending agents, isotonizing agents, buffering agents, and soothing agents in liquid preparations. In drug preparation, preparation additives such as preservatives, antioxidants, colorants, and sweeteners may be used as necessary.

Examples of excipients include lactose, sucrose, D-mannitol, D-sorbitol, starch, pregelatinized starch, dextrin, crystalline cellulose, low-substituted hydroxypropylcellulose, carboxymethylcellulose sodium, gum arabic, pullulan, soft silicic anhydride, synthetic aluminum silicate, magnesium aluminometasilicate, xylitol, sorbitol, and erythritol.

Examples of lubricants include magnesium stearate, calcium stearate, talc, colloidal silica, and polyethylene glycol 6000.

Examples of binders include pregelatinized starch, sucrose, gelatin, gum arabic, methylcellulose, carboxymethylcellulose, carboxymethylcellulose sodium, crystalline cellulose, sucrose, D-mannitol, trehalose, dextrin, pullulan, hydroxypropylcellulose, hydroxypropylmethylcellulose, and polyvinylpyrrolidone.

Examples of disintegrants include lactose, sucrose, starch, carboxymethylcellulose, carboxymethylcellulose calcium, croscarmellose sodium, carboxymethyl starch sodium, low-substituted hydroxypropylcellulose, soft silicic anhydride, and calcium carbonate.

Examples of solvents include water for injection, physiological saline, Ringer's solution, alcohol, propylene glycol, polyethylene glycol, sesame oil, corn oil, olive oil, and cottonseed oil.

Examples of solubilizing agents include polyethylene glycol, propylene glycol, D-mannitol, trehalose, benzyl benzoate, ethanol, tris-aminomethane, cholesterol, triethanolamine, sodium carbonate, sodium citrate, sodium salicylate, and sodium acetate.

Examples of suspending agents include surfactants such as stearyltriethanolamine, sodium laurylsulfate, laurylaminopropionic acid, lecithin, benzalkonium chloride, benzethonium chloride, and glyceryl monostearate; hydrophilic polymers such as polyvinyl alcohol, polyvinyl pyrrolidone, carboxymethylcellulose sodium, methylcellulose, hydroxymethylcellulose, hydroxyethylcellulose, and hydroxypropylcellulose; polysorbates, and polyoxyethylene hydrogenated castor oil.

Examples of isotonizing agents include sodium chloride, glycerin, D-mannitol, D-sorbitol, glucose, xylitol, and fructose.

Examples of buffering agents include buffers such as phosphate, acetate, carbonate, and citrate.

Examples of soothing agents include propylene glycol, lidocaine hydrochloride, and benzyl alcohol.

Examples of preservatives include paraoxybenzoic acid esters, chlorobutanol, benzyl alcohol, phenethyl alcohol, dehydroacetic acid, and sorbic acid.

Examples of antioxidants include sulfite and ascorbate.

Examples of colorants include water-soluble colored tar dyes (e.g., edible dyes such as Food Red Nos. 2 and 3, Food Yellow Nos. 4 and 5, and Food Blue Nos. 1 and 2), insoluble lake dyes (e.g., aluminum salts of the water-soluble edible tar dyes), and natural dyes (e.g., (3-carotene, chlorophyll, and red iron oxide).

Examples of sweeteners include saccharin sodium, dipotassium glycyrrhizinate, aspartame, and stevia.

In addition, it is desirable to use a route of administration which is most effective in treatment, and the tumor therapeutic agent can be administered in the form of oral preparations, injections, or transdermal preparations. Examples of oral preparations include tablets (including sublingual tablets and oral disintegrants), capsule agents (including soft capsules and microcapsules), powders, granules, lozenges, syrups, emulsions, and suspensions. Examples of injections include intradermal injections, subcutaneous injections, intravenous injections, intramuscular injections, intrathecal injections, epidural injections, and local injections. In addition, examples of transdermal preparations include patches, ointments, and dusting powders. These preparations may be release-controlled preparations such as immediate-release preparations or sustained-release preparations (e.g., sustained-release microcapsules).

Synthetic Method

The lenvatinib derivative of the present invention can be manufactured, for example, through the synthetic pathway shown in FIG. 1.

Specifically, compound 4-2 (4-amino-2-methoxybenzonitrile) is obtained by replacing chlorine of starting material 4-1 (4-amino-2-chlorobenzonitrile) with a methoxy group by sodium methylate. Further, ethoxymethylene Meldrum's acid obtained by heating Meldrum's acid and ethyl orthoformate in ethanol reacts additionally with the amino group of compound 4-2 to produce compound 4-3.

Then, compound 4-3 is thermally cyclized to give a quinolone structure of compound 4-4, and nitrile is hydrolyzed to be converted into a carboxylic acid group, thereby giving compound 4-5. Then, compound 4-5 is reacted with a chlorinating agent to cause conversion of the carboxylic acid at the 6-position into an acid chloride, chlorination at the 4-position, and formation of quinoline ring, thereby giving compound 4-6. A nitric acid ester is introduced by an amidation reaction between acid chloride 4-6 and an aminoalkyl nitric acid ester, thereby giving compound 4-7 (see JP S52-122373 A and Indian Journal of Pharmaceutical Sciences, pp. 304-305, 1999). Nucleophilic substitution of chlorine at the 4-position of compound 4-7 with 4-amino-3-chlorophenol gives compound 4-8, followed by carbamation of the amino group to give compound 4-9. Further, compound 4-9 is reacted with cyclopropylamine into a urea substance, thereby giving compound 4-10 which is the lenvatinib derivative of the present invention.

The 4-chloroquinoline derivative (compound 4-6 in FIG. 1) as an intermediate in this synthetic pathway can also be synthesized by a conventional chemical reaction means as described in Organic Synthesis Collective Vol. III, pp. 272-275, 1955; US 2004/053908 A; WO 1998/047873; WO 2000/043366, etc.

The aminoalkyl nitric acid ester can be manufactured using a commercially available aminoalkyl alcohol as a raw material by the following methods 1) to 3), in accordance with the exemplary methods for synthesis of 2-aminoethyl nitric acid ester described in DE1931/514955 and Indian Journal of Pharmaceutical Sciences, pp. 304-305, 1999.

1) Reaction between aminoalkyl alcohol and high-concentration nitric acid (fuming nitric acid)

[Chemical Formula 5]

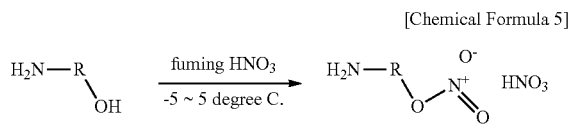

(wherein R represents an alkylene group which may have a branch.)

2) Method involving preparation of mononitrate of aminoalkyl alcohol followed by esterification thereof with high-concentration nitric acid

[Chemical Formula 6]

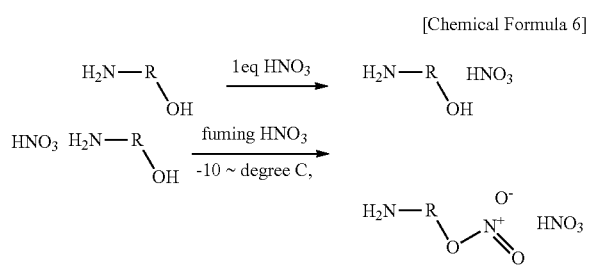

(wherein R represents an alkylene group which may have a branch.)

3) Protection of amino group of aminoalkyl alcohol with phthalic anhydride and nitric acid esterification with concentrated sulfuric acid-fuming nitric acid An aminoalkyl alcohol and phthalic anhydride are reacted with each other to form a phthalimide substance with which the amino group of the aminoalkyl alcohol is protected. Then, nitric acid esterification is carried out with concentrated sulfuric acid-fuming nitric acid, and, after deprotection with hydrazine, an aminoalkyl nitric acid ester in a free form is obtained.

In the synthetic pathway shown in FIG. 1, the amino group of compound 4-8 is carbamated, and then the resultant compound is reacted with an amine into a urea substance. Alternatively, a urea substance may be formed by a reaction of compound 4-8 a) with an amine under basicity in the presence of triphosgene or b) with an isocyanate compound.

Figure 2:
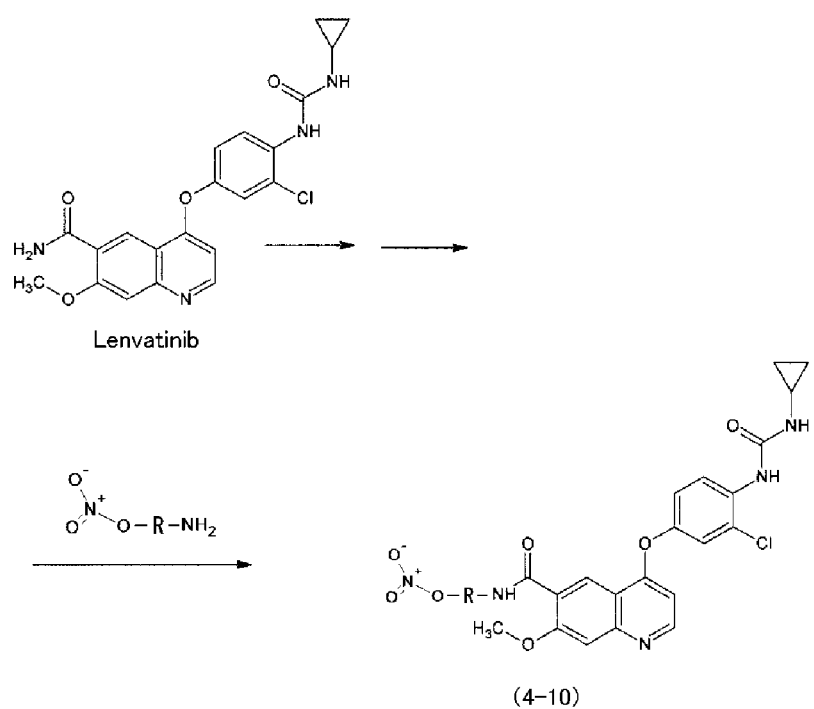
FIG. 2 is a diagram showing another synthetic pathway of the lenvatinib derivative (4-10) of the present invention.

Furthermore, it is possible to synthesize compound 4-10 by conversion from lenvatinib into a nitric acid ester substance. For example, it is also possible to hydrolyze amide substance into a carboxylic acid shown in FIG. 2 and then to convert the carboxylic acid into an acid halide which is reacted with an aminoalkyl nitric acid ester to produce compound 4-10. OR the carboxylic acid is reacted with an aminoalkyl nitric acid ester and a condensation agent such as dichlorohexylcarbodiimide (DCC) to form compound 4-10.

Action Mechanism and Effect

Figure 3:
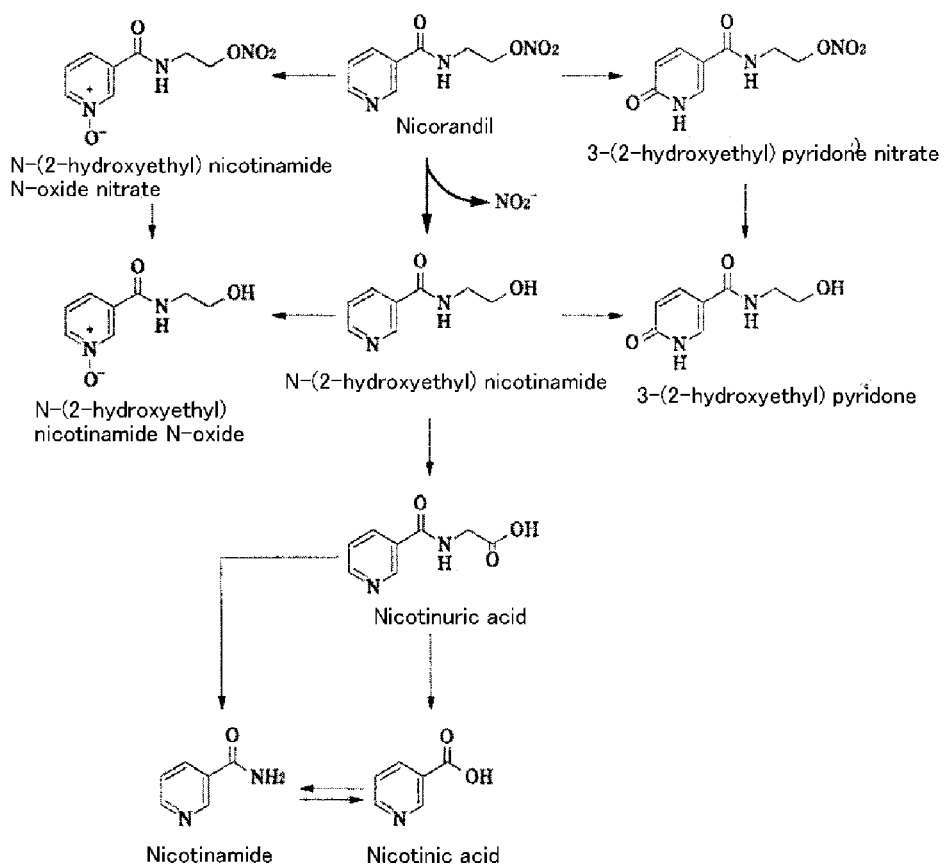
FIG. 3 is a diagram showing in vivo metabolic pathways of nicorandil.

It has been suggested that the compound nicorandil having a nitric acid ester group, similarly to compound 4-10 which is the lenvatinib derivative of the present invention, is present as nicotinamide and the like in the liver and further is converted into endogenous substances NAD and NADP, which are incorporated into a living body, as shown in FIG. 3, from a test of single intravenous administration of 3 mg/kg of $^{14}$C-labeled nicorandil to guinea pigs (see the interview form of "SIGMART tablets 2.5 mg, 5 mg (Nicorandil tablets)" manufactured by Chugai Pharmaceutical Co., Ltd.).

Figure 4:
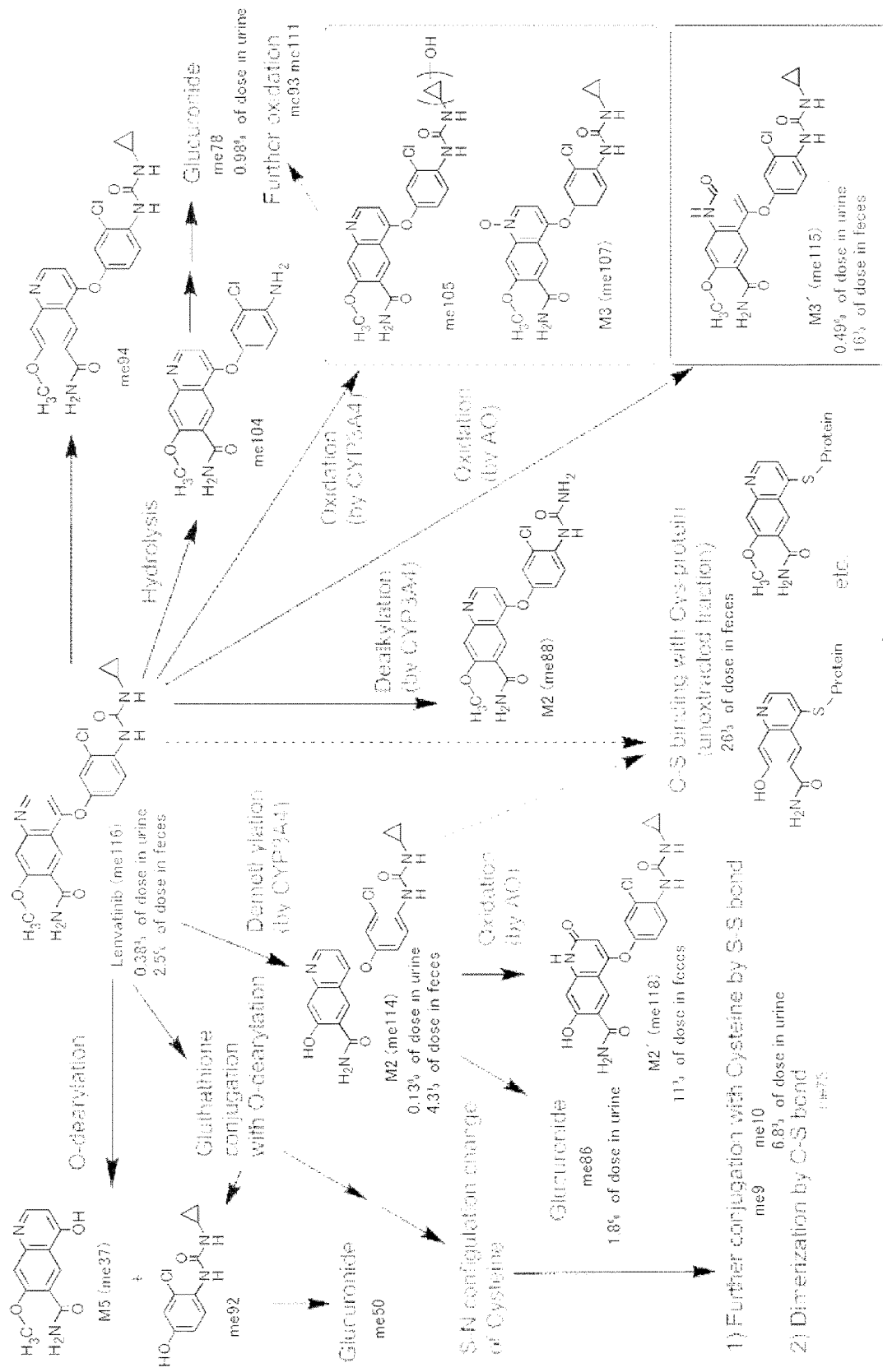
FIG. 4 is a diagram showing presumed in vivo metabolic pathways of lenvatinib.

Also, conventionally, the metabolic cycles shown in FIG. 4 are presumed as the metabolic pathways of lenvatinib.

Figure 5:
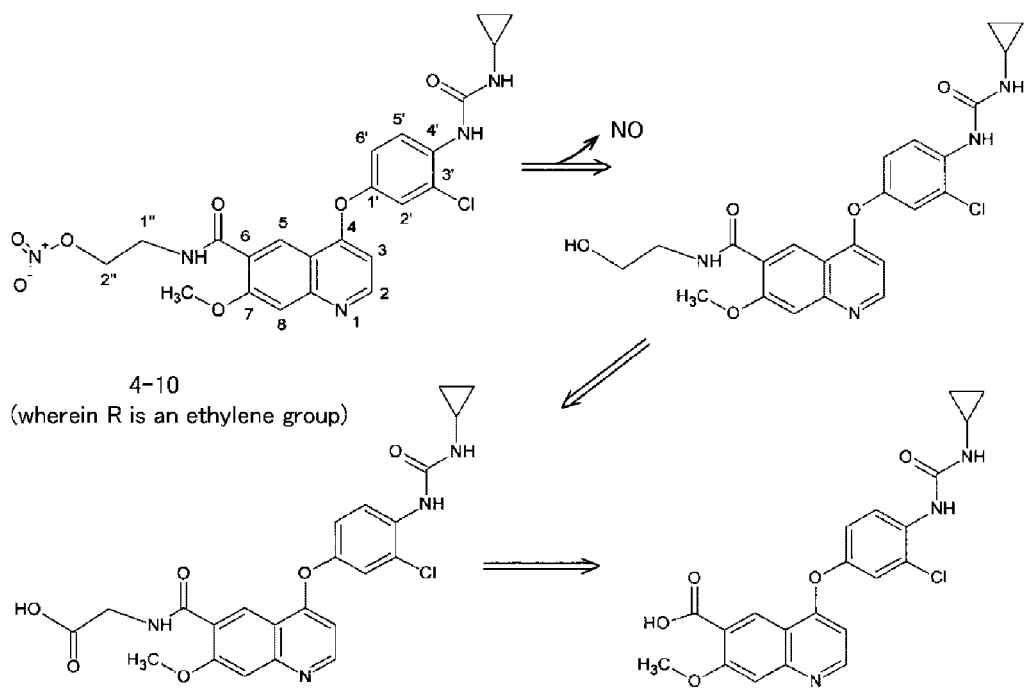
FIG. 5 is a diagram showing presumed in vivo metabolic pathways of the lenvatinib derivative (4-10) of the present invention.

Referring to the above metabolic pathway diagrams, the metabolic stage shown in FIG. 5 is estimated for the nitric acid ester group moiety in compound 4-10 (wherein R is an ethylene group) which is the lenvatinib derivative of the present invention (the same applies even when R is any other alkylene group).

When this lenvatinib derivative is administered, the nitric acid ester group is decomposed in vivo to produce nitric oxide (NO), which dilates blood vessels and lowers blood pressure. On the other hand, the remaining portion where the nitric acid ester group has been decomposed is estimated to be a metabolite similar to the metabolite of lenvatinib, and provides an effect of suppressing the proliferation of cancer cells, which is the medicinal effect of lenvatinib. The vasodilating action obtained by NO increases blood flow, so that a higher-concentration lenvatinib derivative can arrive at target molecules present in cancer cells and vascular endothelial cells on the host side. As a result, a high cancer therapeutic effect can be obtained.

It serves also as a raw material for a pharmaceutical research composition suitable for studying the action mechanism of lenvatinib, such as investigation of the relationship with NO in the in vivo action of lenvatinib.

The present invention is not limited to the above embodiments and examples of the invention at all. Various modifications are also included in the present invention as long as they can be easily conceived by those skilled in the art without departing from the scope of the claims.

The present invention can be used in the medical industry as a tumor therapeutic agent with less hypertension as a side effect. It is also useful as a drug tool for elucidating the action mechanism of lenvatinib to help further development of new drugs.

What is claimed is:

1. A lenvatinib derivative represented by chemical structural formula (1) (wherein R represents an alkylene group which may have a branch) and a salt thereof, and a solvate thereof,

[Chemical Formula 1]

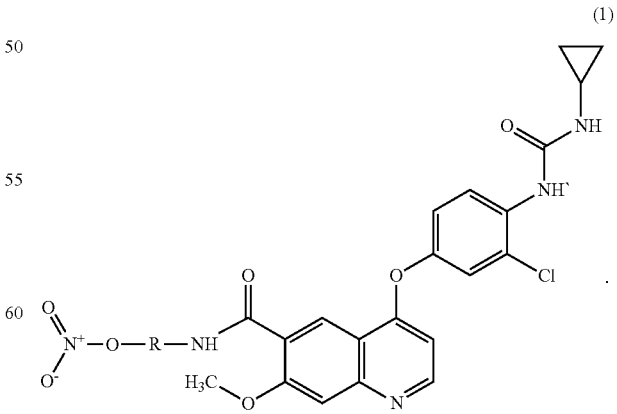

2. A composition comprising the lenvatinib derivative according to claim 1 as an active ingredient, and one or more pharmaceutical acceptable carriers.

3. A tumor therapeutic agent comprising the lenvatinib derivative according to claim 1 as an active ingredient.

\* \* \* \* \*